(12) United States Patent
Bensebaa

(10) Patent No.: US 9,738,868 B2
(45) Date of Patent: Aug. 22, 2017

(54) PHOTOBIOREACTOR

(75) Inventor: Farid Bensebaa, Ottawa (CA)

(73) Assignee: National Research Council of Canada, Ottawa, ON (*) Notice: Subject to any disclaimer, the term of this patent is extended or adjusted under 35 U.S.C. 154(b) by 65 days.

(21) Appl. No.: 14/232,006

(22) PCT Filed: Jul. 4, 2012

(86) PCT No.: PCT/CA2012/000635
§ 371 (c)(1),
(2), (4) Date: Jan. 10, 2014

(87) PCT Pub. No.: WO2013/010252
PCT Pub. Date: Jan. 24, 2013

(65) Prior Publication Data
US 2014/0170726 A1   Jun. 19, 2014

Related U.S. Application Data

(60) Provisional application No. 61/509,277, filed on Jul. 19, 2011.

(51) Int. Cl.
*C12N 1/12* (2006.01)
*C12M 1/00* (2006.01)
(Continued)

(52) U.S. Cl.
CPC .............. *C12N 1/12* (2013.01); *C12M 21/02* (2013.01); *C12M 23/06* (2013.01); *C12M 23/20* (2013.01);
(Continued)

(58) Field of Classification Search
CPC ...... C12M 21/02; C12M 23/06; C12M 31/10; C12M 31/02; C12M 31/08; C12M 31/12;
(Continued)

(56) References Cited

U.S. PATENT DOCUMENTS 988,104 A * 3/1911 Jenckes ........................ 313/513
4,703,010 A * 10/1987 Yunker et al. ............. 435/173.8
(Continued)

FOREIGN PATENT DOCUMENTS

CA   2394518   5/2012
GB   13578    0/1905
(Continued)

OTHER PUBLICATIONS

Au SH, Shih SCC, Wheeler AR. (2001) Integrated microbioreactor for culture and analysis of bacteria, algae and yeast. Biomed Microdevices. 13, 41-50.

(Continued)

*Primary Examiner* — Michael Hobbs
(74) *Attorney, Agent, or Firm* — Christian Berube

(57) ABSTRACT

In the present invention, a photobioreactor and process for producing and harvesting microalgae involves a vessel for cultivating microalgae that is at least partially transparent to admit light into the vessel. At least a portion of the transparent part of the vessel is coated with a transparent conductive oxide (TCO) layer. The TCO layer is transparent to visible light necessary for algae growth, but is opaque to infrared light thereby reducing thermal heating load in the photobioreactor. The TCO layer also acts as an electrode, which when combined with a counter-electrode can provide a potential difference across at least a portion of the interior of the vessel between the TCO layer and the counter-electrode. The electrode arrangement can be utilized in an electrochemical process (e.g. electrodeposition and/or electroflotation) to dewater and harvest the microalgae in the same apparatus as the microalgae was cultivated.

19 Claims, 4 Drawing Sheets

(51) Int. Cl.
  *C12M 1/12* (2006.01)
  *C12M 1/26* (2006.01)
(52) U.S. Cl.
  CPC ............ *C12M 23/22* (2013.01); *C12M 33/00* (2013.01); *C12M 47/02* (2013.01)
(58) Field of Classification Search
  CPC .......... C12M 43/06; C12M 43/08; C02F 3/32; C12N 1/12; C12N 1/10; C12N 1/20; C12N 13/00; C12P 5/023; C12P 7/649; A01G 33/00; Y02E 50/13; Y02E 50/343
  USPC ........................................ 435/292.1; 47/1.4
  See application file for complete search history.

(56) References Cited

U.S. PATENT DOCUMENTS

| | | | |
|---|---|---|---|
| 4,970,166 | A | 11/1990 | Mori |
| 5,134,070 | A | 7/1992 | Casnig |
| 6,001,617 | A | 12/1999 | Raptis |
| 6,509,188 | B1 | 1/2003 | Trosch et al. |
| 6,555,365 | B2 | 4/2003 | Barbera-Guillem et al. |
| 7,354,770 | B2 | 4/2008 | Huebner et al. |
| 7,700,459 | B2 | 4/2010 | Kameyama et al. |
| 7,892,495 | B2 | 2/2011 | Huebner et al. |
| 7,919,319 | B2 | 4/2011 | Jervis et al. |
| 8,091,510 | B2 | 1/2012 | Hughes |
| 2002/0072113 | A1 | 6/2002 | Barbera Guillem et al. |
| 2006/0174938 | A1 | 8/2006 | Di Palma et al. |
| 2007/0161106 | A1 | 7/2007 | Jervis et al. |
| 2008/0156658 | A1 | 7/2008 | Herrington et al. |
| 2008/0213632 | A1 | 9/2008 | Noguera et al. |
| 2008/0268302 | A1 | 10/2008 | McCall |
| 2009/0221025 | A1 | 9/2009 | Huebner et al. |
| 2010/0009335 | A1 | 1/2010 | Joseph et al. |
| 2010/0068791 | A1 | 3/2010 | Merimon et al. |
| 2010/0133110 | A1* | 6/2010 | Nocera et al. ................ 205/340 |
| 2010/0162621 | A1 | 7/2010 | Seebo |
| 2010/0255569 | A1 | 10/2010 | Camarate de Albuquerque |
| 2010/0304458 | A1 | 12/2010 | Bombelli |
| 2011/0117635 | A1 | 5/2011 | Sen |
| 2013/0092237 | A1* | 4/2013 | Takshi .................... H01M 8/16 136/263 |

FOREIGN PATENT DOCUMENTS

| | | |
|---|---|---|
| WO | 2007/092571 A3 | 8/2007 |
| WO | 2008/118500 A1 | 10/2008 |
| WO | 2010/123903 A1 | 10/2010 |

OTHER PUBLICATIONS

Dye D, Muhs J, Wood B, Sims R. (2010) Design and Performance of a Solar Photobioreactor Utilizing Spatial Light Dilution. Proceedings of the ASME 2010 4th International Conference on Energy Sustainability. ES 2010-90191, 1067-1076.

Poelman E. De Pauw N. Jeurissen B. (1997) Potential of electrolytic flocculation for recovery of micro-algae. Resources, Conservation and Recycling. 19, 1-10.

Posten C. (2009) Design principles of photo-bioreactors for cultivation of microalgae. Eng. Life Sci. 9(3), 165-177.

Su Z, Kang R, Shi S, Cong W, Cai Z. (2010) An Effective Device for Gas—Liquid Oxygen Removal in Enclosed Microalgae Culture. Appl Biochem Biotechnol. 160, 428-437.

Uduman N, Qi Y, Danquah MK, Forde GM, Hoadley A. (2010) Dewatering of microalgal cultures: A major bottleneck to algae-based fuels. Journal of Renewable and Sustainable Energy. 2, 012701.

Xu L, Wang F, Li H-Z, Hu Z-M, Guob C, Liub C-Z. (2010) Development of an efficient electroflocculation technology integrated with dispersed-air flotation for harvestingmicroalgae. J Chem Technol Biotechnol. 85, 1504-1507.

Xuan DTT. (2009) Harvesting marine algae for biodiesel feedstock. Report of 8 pages.

Yang Ryk, Bayraktar O, Pu HT. (2003) Plant-cell bioreactors with simultaneous electropermeabilization and electrophoresis. Journal of Biotechnology. 100, 13-22.

International Search Report/Written Opinion for PCT/CA2012/000635 dated Oct. 1, 2012.

Liu, H. et al. Transparent conducting oxides for electrode applications in light emitting and absorbing devices. Superlattices and Microstructures. Nov. 2010. vol. 48, No. 5, pp. 458-484, ISSN 0749-6036.

* cited by examiner

PHOTOBIOREACTOR

CROSS-REFERENCE TO RELATED APPLICATIONS

This application is a national entry of International Patent Application PCT/CA2012/000635 filed Jul. 4, 2012 and claims the benefit of United States Provisional Patent application U.S. Ser. No. 61/509,277 filed Jul. 19, 2011, the entire contents of both of which are herein incorporated by reference.

FIELD OF THE INVENTION

The present application is related to apparatuses and processes for producing and harvesting microalgae.

BACKGROUND OF THE INVENTION

Depleting cheap fossil fuel reserves and a pressing need for greenhouse gas (GHG) emission reduction are two major technico-economic challenges. Thus, it is quite urgent to develop cost effective, clean and renewable sources for both energy and chemical needs. Microalgae is actively investigated as a long term solution to cover these needs. Microalgae has a potential of producing up to 4,000 Gallons of oil per acre per year. This production rate is more than an order of magnitude higher than any other biofuel source. However currently used production and harvesting processes of microalgae are energy intensive and relatively costly. Except for a few high value nutrients, proteins and other byproducts, microalgae based biofuels are not commercially viable. Furthermore, current energy intensive harvesting processes give rise to significant $CO_2$ emissions.

There are five important processing steps required to obtain biofuels and/or chemicals from microalgae. Step #1 involves cultivating microalgae to produce more microalgae. Following the cultivation step, microalgae is collected and dewatered in Step #2 leading to concentrated dilute microalgal suspensions having TSS (total solid suspensions) content in a range from 0.5 to 5%. More extensive dewatering process combining one or more techniques that include centrifugation, flocculation, filtration and screening, gravity sedimentation, flotation and electrophoresis increases the TSS content up to around 10-20% TSS (Step #3). In Step #4, a drying process gives rise to a TSS of at least 25%. In the last step (Step #5), extraction processes are undertaken to produce the final product. In some cases, product extraction may be undertaken before the drying step. For example, in the case of anaerobic digestion primary dewatering is sufficient.

Following the cultivation step using a photobioreactor, the yield is often in the range of a maximum of about 1 kg dry weight/day/m$^3$. The average TSS content is about 0.05% (Step #1). The large amount of water comprises extracellular and intracellular water. Depending on the requirements for drying (Step #4) and extraction (Step #5) and the targeted list of final products and byproducts, intracellular water removal may take place at different stages.

Different processing technologies are used for transforming the slurry to a sludge/cake and then to a dry state. Depending on the dewatering process, these industrial processes may also give rise to low specific production yield. The yield of these dewatering processes should be high while using minimum amount of energy.

A drying process that allows the completion of the harvesting process could increase the TSS content to about 75%. Dehydration faces two challenges related to algae degradation and loss of valuable chemicals and high energy cost. In the case of extraction, the following processes are often used: mechanical crushing (expeller press), solvent (hexane, benzene) extraction, supercritical $CO_2$, enzymatic hydrolysis, microwave, cavitation and cellular decompression.

Three different algae cultivation methods are used including raceway pond, tubular photobioreactor and flat plate photobioreactor. Raceway pond has the lowest capital cost with the lowest energy input. However raceway pond uses significant land area and water with poor biomass productivity. Furthermore, raceway pond systems are limited to a few strains of algae with less control over the cultivation conditions. A photobioreactor can be generally described as an enclosed, illuminated culture vessel designed for controlled biomass production of phototrophic liquid cell suspension cultures. Tubular photobioreactors have been developed to increase biomass productivity by providing a large specific illumination surface area and more control of cultivation conditions. Capital cost of tubular reactors is relatively higher than raceway pond. They also present several challenges related to fouling, presence of oxygen and $CO_2$, and gradients of pH values. They require large land area, although less than the raceway pond. In the third method, flat plate photobioreactors provide the highest biomass productivity, although illumination conditions are less than optimal. Flat plate photobioreactors are cheaper to produce, but they are difficult to scale-up with significant temperature control challenges. Per unit mass of produced algae, flat plate photobioreactors are cost effective.

Cultivation and dewatering represent two significant challenges for implementing commercial processes. These steps are critical for implementing an algae-based manufacturing of chemicals (nutrients, proteins) and biofuel (biodiesel) products. Unless the financial and energy costs of these two steps are significantly reduced, the commercial viability of biodiesel-based microalgae is questionable. However, high value byproducts such as nutrients and protein obtained from microalage are currently commercially viable.

The majority of dewatering techniques are based on water removal from the algae suspension. Electrochemical processes including electrodeposition (ED), electrocoagulation (EC), electroflotation (EF) and electrooxidation (EO) could be used for algae removal. Reducing the energy cost in the algae dewatering and drying processes while maintaining high yield output are commercially important. For example, electroflotation presents several attributes for large scale algae removal. Indeed, large scale algae removal from waste using electroflotation has been demonstrated. They do not require additional chemical flocculants or a sacrificial electrode and give rise to high yield (90% or more). Adding chemicals makes the downstream processes even more complicated and expensive. Electrodeposition and electroflotation face other specific challenges related mostly to additional capital cost.

Combining two or more of the processing steps discussed above into a single step would not only reduce capital cost but would also reduce cost of operation and maintenance (O&M). In particular, combining cultivation and dewatering using a single apparatus and/or process could allow high production yield with reduced production cost.

There remains a need for a photobioreactor design and process that meets one or more of the aforementioned challenges.

SUMMARY OF THE INVENTION

In one aspect of the present invention, there is provided a photobioreactor for producing and harvesting microalgae, the photobioreactor comprising: a vessel for cultivating microalgae, the vessel having at least one wall and an interior, at least a portion of the at least one wall being transparent to permit light of a frequency necessary to promote microalgae growth to enter into the interior of the vessel, at least part of the transparent portion of the at least one wall comprising a layer of transparent conductive oxide for use as an electrode, the transparent conducting oxide being transparent to light of the frequency necessary to promote microalgae growth and opaque to light of an infrared frequency range; and, a counter-electrode electrically connected to the layer of transparent conductive oxide for providing a potential difference across at least a portion of the interior of the vessel between the layer of transparent conductive oxide and the counter-electrode.

In another aspect of the present invention, there is provided a process for producing and harvesting microalgae in a single apparatus, the process comprising: cultivating microalgae on a cell culture medium in a vessel of a photobioreactor, the vessel having at least one wall and an interior, at least a portion of the at least one wall being transparent to permit light of a frequency necessary to promote microalgae growth to enter into the interior of the vessel, at least part of the transparent portion of the at least one wall comprising a layer of transparent conductive oxide for use as an electrode, the transparent conducting oxide being transparent to light of the frequency necessary to promote microalgae growth and opaque to light of an infrared frequency range; and, dewatering the microalgae electrochemically by applying a potential difference across at least a portion of the interior of the vessel between the layer of transparent conductive oxide and a counter-electrode electrically connected to the layer of transparent conductive oxide.

Microalgae, or microphytes, are microscopic, photosynthetic algae that may be found in freshwater or marine systems. They are unicellular, existing individually or in chains or groups. Depending on species, their sizes can range from about 0.1 micrometer to a few hundreds of micrometers. Microalgae are important industrially since they are capable of producing unique bio-products, for example, carotenoids, antioxidants, fatty acids (e.g. omega-3-fatty acids), enzymes, polymers, peptides, fuels, toxins and sterols. Any suitable species of algae may be cultivated in the photobioreactor, the choice of which depends on the type of bio-product that is desired to be produced. *Chlorella*, *Dunaliella* and *Nannochloropsis* are few examples of microalgae that could be used in the present photobioreactors. Cultivation occurs in a cell culture medium comprising necessary nutrients and factors for algae growth. Such nutrients and factors are well known in the art and depend on the species of algae being cultivated.

Any suitable basic design for the photobioreactor may be used, for example, tubular or flat plate photobioreactors. Tubular photobioreactors generally comprise a cylindrical vessel having a curved outer wall at least a portion of which is transparent. Flat plate photobioreactors generally comprise at least two opposed outer walls, at least part of at least one of which is transparent. Whatever the basic design, the photobioreactor comprises a vessel within which the microalgae is cultivated. The vessel comprises walls for containing the microalgae and the cell culture medium. Since microalgae are photosynthetic organisms, they require light in order to grow and reproduce. The light is generally of a frequency in the visible region of the electromagnetic spectrum. In order to permit light to enter the vessel, at least a portion of at least one wall of the vessel is transparent. Transparency may be attained by constructing the transparent portion of the vessel from a transparent material, for example, glass, plastic, fiber glass or mixtures thereof. More light can be permitted to enter the vessel by increasing the surface area of the transparent portion in relation to the total surface area of the vessel. If desired, the entire vessel may be constructed from transparent material. The wall of the vessel for which at least a portion is transparent is preferably an outer wall of the vessel.

At least part of the transparent portion of the at least one wall comprises a layer of transparent conductive oxide (TCO) for use as an electrode. In photobioreactor designs where the entire vessel is transparent, it is possible for the TCO layer to cover the entire photobioreactor, although the exact surface area of the TCO layer depends on design considerations. The TCO layer is preferably on the inside of the vessel surface.

In thin layers, transparent conducting oxides are optically transparent to visible wavelengths (380 nm to 750 nm) and are electrically conductive. They have been typically used in electronic applications, for example microelectronics, photonics (e.g. solar cells) and architecture windows. Some examples of TCOs include indium doped tin oxide (ITO), fluorine doped tin oxide (FTO), antimony doped tin oxide (ATO), zinc doped tin oxide (ZTO), aluminum doped zinc oxide (AZO) or mixtures thereof. TCO layers typically have a thickness in a range of from about 0.01 µm to about 100 µm. The preferred thickness is in a range of from about 0.1 µm to about 10 µm.

About 45% of solar radiation, which is typically used as the light source for photobioreactors, comprises infrared light. Infrared light does not contribute to the photosynthetic process in microalgae, however, infrared light does contribute to increased temperature and radial thermal gradient in the photobioreactor. Such thermal heating under solar load makes temperature control in the vessel difficult leading to over-heating and algae death, thus reducing production yield. While transparent conducting oxides are optically transparent to visible wavelengths, they are opaque to infrared wavelengths. Thus, the TCO layer blocks at least a portion of the infrared region of solar radiation mitigating against thermal heating in the photobioreactor while transmitting the visible portion to be used by the microalgae in the photosynthetic process. This is a major advantage in photobioreactor design.

The transparent conducting oxide (TCO) layer also functions as an electrode. When coupled with a counter-electrode, a potential difference can be generated across at least a portion of the interior of the vessel between the transparent conductive oxide layer and the counter-electrode. This permits application of electrochemical processes to harvest the microalgae growing in the vessel. The counter-electrode may be a layer on another wall of the vessel, or it may be an electrode placed somewhere in the interior of the vessel. The counter-electrode may comprise any suitable electrically conductive material, for example a metal (e.g. aluminum, stainless steel, etc.), a conductive carbon, a transparent conducting oxide (TCO) or a mixture thereof. If the counter-electrode comprises a TCO, the TCO of the counter-electrode may be the same or different as the TCO in TCO layer. If the counter-electrode is metal-based and is to be placed within the vessel where it is in contact with the microalgae and other contents of the vessel, it may be advantageous to coat the counter-electrode with an inert coating, for example a fluorine-type coating (e.g. polytetrafluoroethylene (PTFE)). For greater efficiency, the counter-electrode preferably has a length that spans the interior of the vessel. The counter-electrode may be fixed or moveable (e.g. rotatable). The potential difference can be generated by applying a voltage between the transparent conductive oxide layer and the counter-electrode. The voltage may be generated by any suitable electrical power source. The two electrodes may be placed in any suitable orientation in the vessel, for example, vertically, horizontally or at some other angle with respect to the direction of earth's gravitational field. The TCO electrode and the counter-electrode may have the same or different orientations with respect to each other. In one embodiment, the counter-electrode is oriented perpendicularly to the orientation of the layer of transparent conductive oxide.

Any number of different electrochemical processes may be applied through the TCO electrode and counter-electrode to facilitate growth, dewatering and/or separation of the microalgae. Electrochemical processes include electrophoretic and/or electrolytic processes, for example water electrolysis, electrodeposition (ED), electrocoagulation (EC), electroflotation (EF) and electrooxidation (EO).

In an embodiment of an electrophoretic process, application of low voltage and low current density across the two electrodes after a complete photosynthesis cycle permits collection and dewatering of the microalgae through electrodeposition. Typically, a voltage in a range of from about 1 V to about 100 V is applied, depending on the algae concentration, pH and the distance between the two electrodes. Negatively charged microalgal cells migrate to the positively polarized electrode (anode) where they form aggregates (flocculates) of microalgae cells at the surface of the anode. The aggregated cells may then be conveniently collected with or without removing the electrode from the vessel. The collected aggregates have much higher solids content than the microalgae during cultivation.

In an embodiment of an electrolytic process, application of a high enough voltage to electrolyze water into hydrogen and oxygen permits the generation of gases that induce turbulence that increases bulk photosynthesis efficiency and algae yield. Oxygen generated at the anode where microalgae flocculation is occurring helps float the microalgae flocculates to the surface of the medium in the vessel via an electroflotation process. Flocculated and floated microalgae cells can then be more conveniently harvested and have a much higher solids content than the microalgae during cultivation. Flocculated and floated microalgae cells may be collected with or without removing the electrode from the vessel. Orienting the anode in a horizontal manner promotes electroflotation.

Thus, the transparent conducting oxide layer can advantageously serve three purposes for cultivating and harvesting microalgae in a single apparatus. It reduces infrared radiation absorption in the photobioreactor facilitating temperature control under high solar radiation load. It permits utilization of electrophoretic techniques to perform dewatering. And, it permits generation of water electrolysis gas to increase bulk photosynthesis efficiency and algae yield and to perform further dewatering by fostering flocculation and floatation of the microalgae.

The photobioreactor may comprise other standard accessories and connections to allow algae growth during cultivation. Such accessories include, for example, means to introduce carbon dioxide, means to introduce water, means to introduce nutrients, means for mixing and means for gas removal (e.g. hydrogen and oxygen removal). Further, membranes may be included between the TCO electrode and counter-electrode to facilitate electrochemical processes. Further, spatial orientation of the photobioreactor may be adjusted to improve mixing of bulk microalgae in the vessel and/or to improve spatio-temporal light distribution in the vessel.

After cultivation and dewatering, microalgae are collected from the anode using any suitable means, for example, mechanically (e.g. scraping) or by dissolving the microalgae in a suitable solvent. Collection may be performed by first removing the anode from the photobioreactor (a batch process) or by collecting the microalgae from the anode without removing the anode from the photobioreactor (a continuous process). The collected microalgae is further dried and then the desired bio-product is recovered. Drying may be accomplished by any suitable means, for example, centrifugation, pressing and filtering. The ultimate drying process includes thermal sources (electrical and/or solar), which could lead to a TSS content in the range of about 75%. Bio-product recovery from the dried microalgae may be accomplished by any suitable means, for example, solvent extraction, anaerobic digestion (a wet process) and pyrolysis (a dry process). Liquids left behind during dewatering and drying may be reused or treated to remove valuable components including nutrients, dissolved bio-products and the like.

Photobioreactors and processes of the present invention using a transparent conducting oxide layer and combining growth and dewatering steps advantageously leads to improved algae yield, reduced capital cost, reduced operating costs and use of fewer added chemicals for flocculation. The present photobioreactors and processes are efficient for producing bio-products using microalgae and solar energy, and also advantageously sequester carbon dioxide.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1:
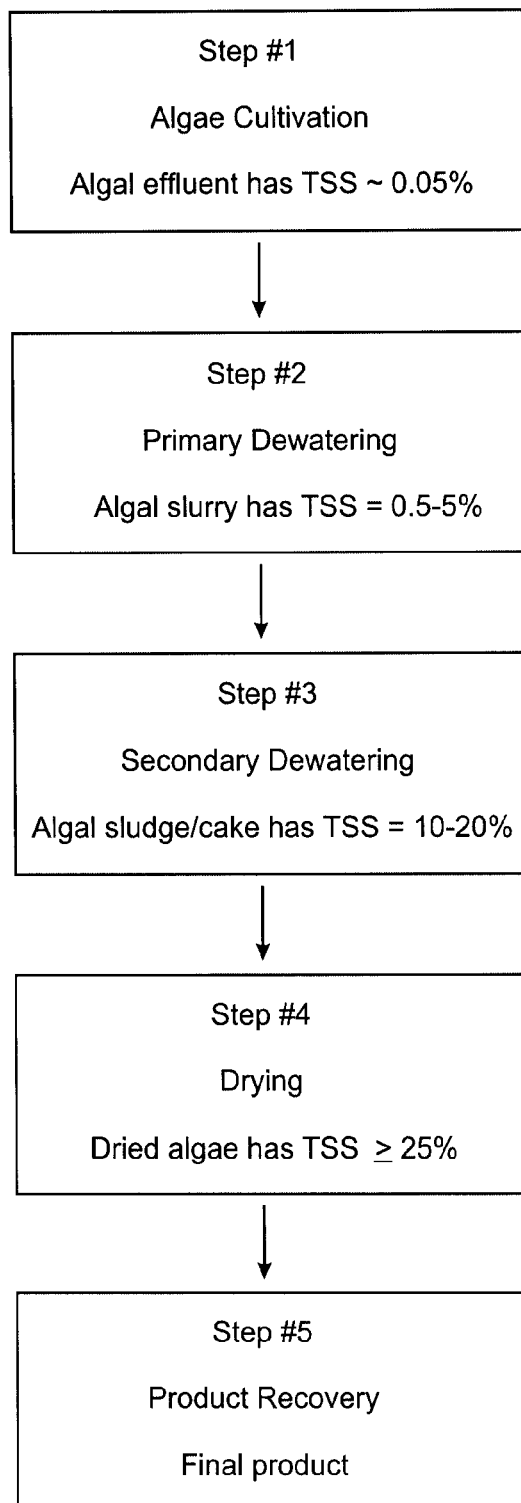
FIG. 1 depicts a simplified microalgae value chain showing steps in a process for obtaining bio-product from microalgae cultivation.

A simplified microalgae value chain showing steps in a process for obtaining bio-product from microalgae cultivation is depicted in FIG. 1. In Step #1, microalgae is cultivated by growing it on a cell culture medium in a photobioreactor. Typically, the total solids content (TSS) of the algal effluent created during cultivation is on the order of about 0.05%. After cultivation to produce quantities of microalgae, the microalgae must be dewatered and harvested. Dewatering typically takes place in a primary dewatering step (Step #2) to produce an algal slurry having a TSS in a range of from about 0.5-5% followed by a secondary dewatering step (Step #3) producing an algal sludge/cake having a TSS in a range of from about 10-20%. Primary and secondary dewatering using electrochemical processes is primarily concerned with removing extracellular water. In the present process, cultivation, primary dewatering and secondary dewatering may all be accomplished in the same apparatus, i.e. the photobioreactor, and the algae harvested only at the end of the secondary dewatering step. The process can therefore be more efficient and cost effective.

After harvesting the algae from the secondary dewatering step, the algae is further dried in Step #4 to provide dried algae having a TSS of about 25% or more. The drying step may further focus on removal of intracellular water. Dried algae can then be processed to recover desired bio-products.

EXAMPLE 1

Tubular Photobioreactor

Figure 2A:
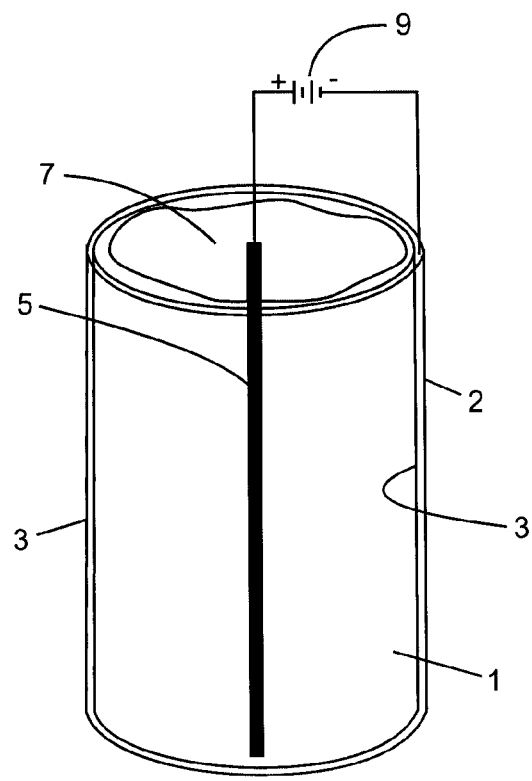
FIG. 2A depicts a schematic representation in plan view of a simplified tubular photobioreactor in accordance with the present invention having a transparent conductive oxide (TCO) layer coated on an outside wall of the photobioreactor, where algae aggregates are collected at the surface of the culture medium.
Figure 2B:
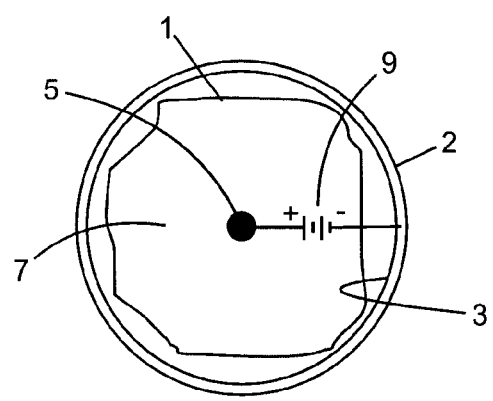
FIG. 2B depicts a schematic representation in top view of the tubular photobioreactor of FIG. 2A.

Referring to FIG. 2, a tubular photobioreactor comprises cylindrical vessel 1 having outer wall 2 made of a transparent plastic that permits solar energy to enter the interior of vessel 1 where the microalgae is being cultivated. Outer wall 2 has a curved inside and outside surface and the inside surface is coated with transparent conducting oxide (TCO) layer 3 comprising fluorine doped tin oxide (FTO). The TCO layer blocks infrared red light from entering the vessel while transmitting visible light. TCO layer 3 also acts as an electrode in an electric circuit further comprising rod-like counter-electrode 5 made from PTFE-coated aluminum and power generator 9 for applying a voltage across the electrodes. Applying low voltage and current across the electrodes after the microalgae production cycle is complete polarizes the electrodes, with TCO layer 3 being a cathode (negative) and counter-electrode 5 being an anode (positive). Since microalgae are slightly negatively charged, the microalgae produced during cultivation are repelled from negatively charged TCO layer 3 on the outside wall of cylindrical vessel 1 and attracted to positively charged anode 5 suspended in the algae culture medium along the full length of and in the center of cylindrical vessel 1. On applying a voltage and current sufficient to electrolyze water, aggregates 7 of microalgal cells are carried to the surface of the culture medium by hydrogen and oxygen gas bubbles formed during water electrolysis. For simplicity, standard photobioreactor accessories and connections are not shown in FIG. 2.

EXAMPLE 2

Flat Plate Photobioreactor

Figure 3:
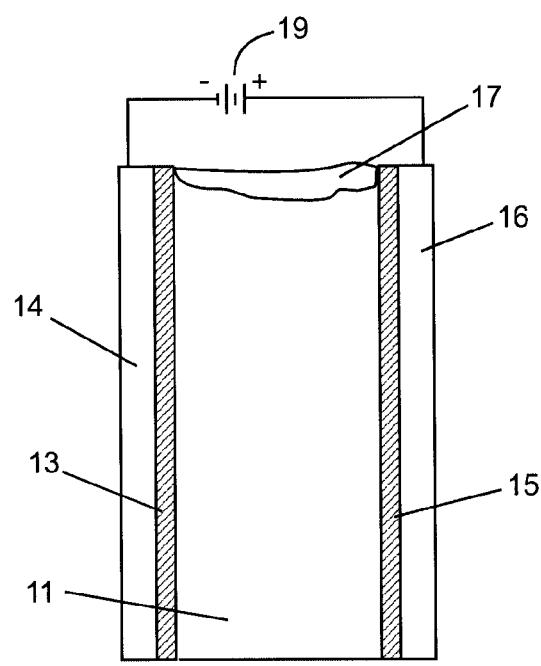
FIG. 3 depicts a schematic representation in side view of a simplified flat plate photobioreactor in accordance with the present invention having a first transparent conductive oxide (TCO) layer coated on an outside wall of a first plate and a second different transparent conductive oxide (TCO) layer coated on an inside wall of a second plate.

Referring to FIG. 3, a flat plate photobioreactor comprises vessel 11 having opposed first outer wall 14 and second outer wall 16 both made of a transparent plastic that permits solar energy to enter the interior of vessel 11 where the microalgae is being cultivated. The inside surfaces of outer walls 14 and 16 are coated with transparent conducting oxide (TCO) layers 13 and 15, respectively, each TCO layer comprising fluorine doped tin oxide (FTO). The TCO layers block infrared red light from entering the vessel while transmitting visible light. TCO layers 13 and 15 also act as electrodes in an electric circuit further comprising power generator 19 for applying a voltage across the electrodes. On applying a voltage and current sufficient to electrolyze water, aggregates 17 of microalgal cells are carried to the surface of the culture medium by hydrogen and oxygen gas bubbles formed during water electrolysis. For simplicity, standard photobioreactor accessories and connections are not shown in FIG. 3.

EXAMPLE 3

Collecting Microalgae Deposits

Aggregates of microalgae cells produced in photobioreactors, generally contain total solids content (TSS) of about 20% and may be collected in any one of a number of different ways. In a batch process, the anode having any aggregates of microalgal cells deposited thereon may be removed from the photobioreactor and the microalgae recovered from the anode either mechanically (e.g. by scraping or skimming) or chemically (e.g. by dissolving in a solvent (e.g. hexanes)). Chemical recovery can further facilitate downstream bio-product extraction. In a continuous process, a skimmer and collection barrel may be added to the photobioreactor.

The continuous process for microalgae harvesting is promoted by electroflotation in which the microalgae aggregates are moved toward the surface of the culture medium. The voltage and current across the electrodes is set to permit electrolysis of water so that oxygen formed at the anode will help flocculate the microalgae and float the flocculates to the surface. Once at the surface, the flocculated microalgae is more easily collected by a skimmer into a barrel. Electroflotation requires little energy and no chemical flocculants. Since oxygen is formed at the anode and hydrogen is also formed at the cathode, the photobioreactor should be equipped with means to remove these gases, especially the oxygen, in order to increase yield of the microalgae. Temperature, pH, current density and anode geometry may be adjusted to achieve a desired oxygen bubble size for more efficient flotation of the microalgae.

Typical operation for both batch and continuous processes is based on 24 hour cycles. During the day microalgae is grown, while at night an electrochemical process is applied to harvest the algae. Thus electricity from off-peak power could be utilized, thereby reducing operating costs. Other operations including changing water and other inputs may also done in the absence of solar radiation. Shorter and longer cycle durations may also be used depending on the microalgae species and other considerations including solar irradiation and microalgae concentration.

EXAMPLE 4

Photobioreactor (PBR) Design for Algae Growth and Harvesting

Comparison Between Plain Glass and TCO-Coated Glass Photobioreactors

A transparent conducting oxide (TCO) coating blocks the infrared (IR) portion of excitation lamps used as the light source for algae growth in the reactor. Thus, the operating temperature of a TCO-coated glass photobioreactor should be lower than that of a plain glass photobioreactor. Further, because a plain glass photobioreactor is expected to operate at a higher temperature (in the absence of additional cooling steps), algae growth rate in the plain glass reactor should also be less than in the TCO-coated glass bioreactor.

Two 9 L photobioreactors (PBRs) were constructed using a flat-plate design, one using plain glass walls (Glass-PBR), and one using TCO-coated glass walls (TCO-PBR), where the TCO layers coated on opposing glass walls act as electrodes for further harvesting of the algae. The TCO layer comprised fluorine doped tin oxide (FTO). A Pavlova strain of algae obtained from MRS (Marine Research Station, NRC Halifax) was cultured in the bioreactors in an aqueous culture medium with carbon dioxide introduced into the culture medium by means of a conduit. The culture medium comprised f/2 stock solution and tris(hydroxymethyl)aminomethane. (tris). The reactors were operated for an extended period of time using the same light source to supply light for algae growth. Two sets of two 60 W G25 soft white bulbs were used. Light was supplied under a normal daily photoregime, and no additional cooling was supplied to either reactor.

Figure 4A:
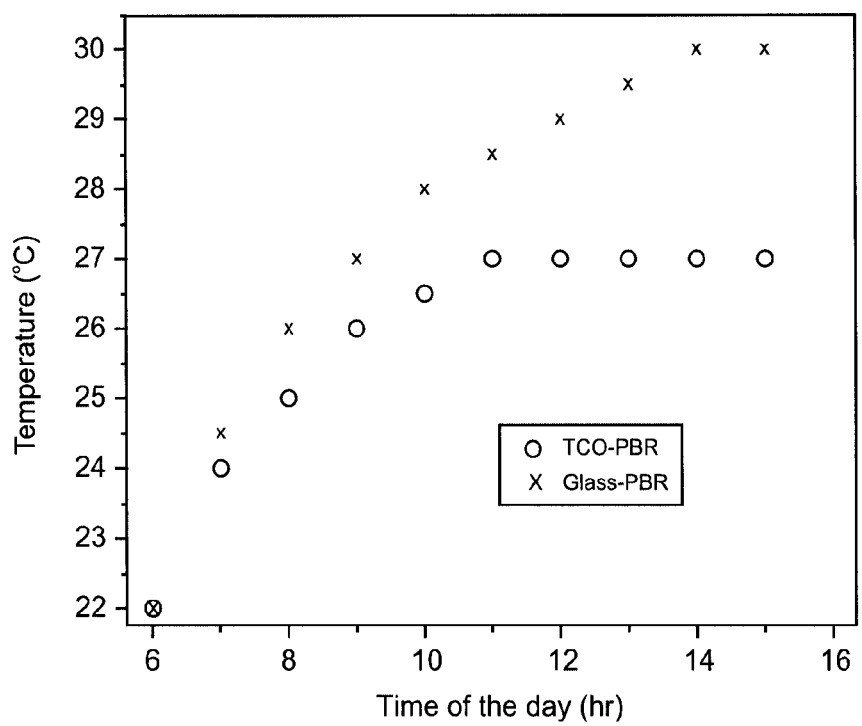
FIG. 4A depicts a graph of temperature (° C.) vs. time of the day (hr) for a photobioreactor constructed from just glass (Glass-PBR) compared to a photobioreactor of the present invention constructed from TCO-coated glass (TCO-PBR); and, FIG. 4B depicts a graph of algae concentration (a.u.) vs. time (hrs) for algae growth in a photobioreactor constructed from just glass (Glass-PBR) compared to a photobioreactor of the present invention constructed from TCO-coated glass (TCO-PBR).
Figure 4B:
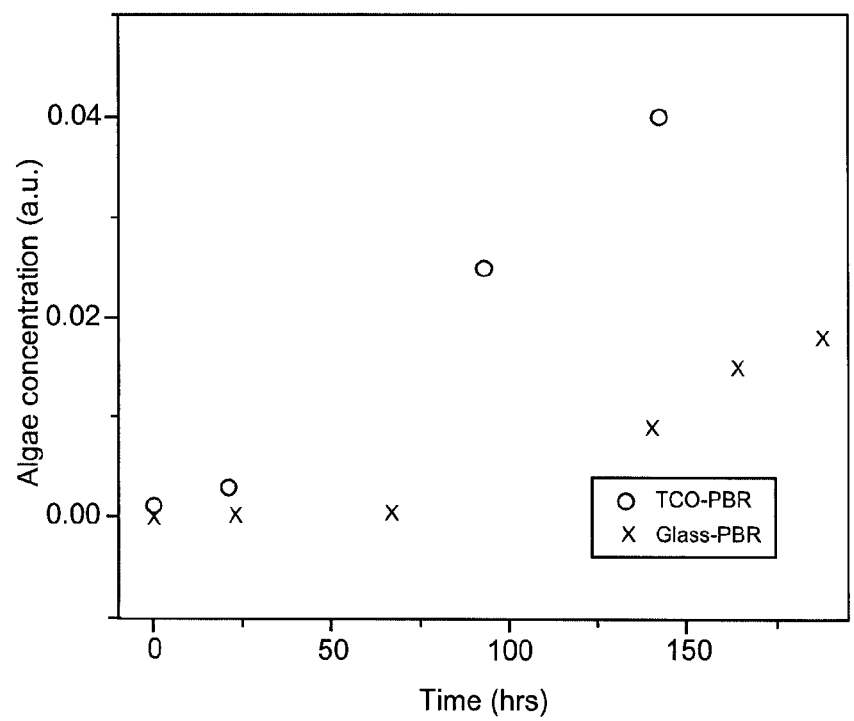

FIG. 4A shows the temperature in each reactor as a function of the time of day, and FIG. 4B shows the concentration of algae as a function of the length of time the photobioreactors are operated. FIG. 4A shows that culture temperature in the Glass-PBR is about 2° C. higher for most of the photo-irradiation period than the temperature in the TCO-PBR. Further, the culture temperature in the Glass-PBR exceeded 27° C. for much of the photo-irradiation period. For most algae strains, operation temperature above 27° C. is detrimental to algae growth, therefore additional cooling is normally required for a Glass-PBR. However, the temperature in the TCO-PBR never exceeded 27° C., thereby reducing cooling requirements normally needed to sustain algae growth in a Glass-PBR. FIG. 4B confirms that algae growth rate obtained using the TCO-PBR is about 2-times faster than what is obtained with the Glass-PBR.

Harvesting

Harvesting of the algae in the TCO-PBR was accomplished by electroflotation using the TCO layers coated on opposing glass walls act as electrodes using a continuous power with 3 volts and 1 amp. Electroflotation harvesting lead to algae concentration of 3.5 wt % (or 35 g/L), which is within the 2-5 wt % concentration range reported in the literature. Concentration of the harvested algae was estimated using a freeze-dry process. The total electric power consumption of this electroflotation harvesting process was less than 0.3 kWh/m$^3$. The low cost and high efficiency of this electroflotation harvesting process is a useful complement to more energy intensive centrifugation processes.

REFERENCES

The contents of the entirety of each of which are incorporated by this reference.

Au S H, Shih S C C, Wheeler A R. (2011) Integrated microbioreactor for culture and analysis of bacteria, algae and yeast. *Biomed Microdevices.* 13, 41-50.

Barbera-Guillem E, Lucas R D. (2002) Microincubator Comprising a Cell Culture Apparatus and a Transparent Heater. United States Patent Publication US 2002-0072113 issued Jun. 13, 2002.

Barbera-Guillem E, Lucas R D. (2003) Microincubator Comprising a Cell Culture Apparatus and a Transparent Heater. U.S. Pat. No. 6,555,365 issued Apr. 29, 2003.

Bombelli P. (2010) Hydrogen and Electrical Current Production from Photosynthetically Driven Semi-Biological Devices (SBDS). United States Patent Publication US 2010-0304458 published Dec. 2, 2010.

Casnig D R. (1992) Method and Device for Cell Cultivation on Electrodes. U.S. Pat. No. 5,134,070 issued Jul. 28, 1992.

Di Palma V, Cimmino A, Scaldaferri R, Carfagna C, De Maria A, Casuscelli V. (2006) Water-based Electrolyte Gel for Dye-sensitive Solar Cells and Manufacturing Methods. United States Patent Publication US 2006-0174938 published Aug. 10, 2006.

Dye D, Muhs J, Wood B, Sims R. (2010) Design and Performance of a Solar Photobioreactor Utilizing Spatial Light Dilution. *Proceedings of the ASME* 2010 4$^{th}$ *International Conference on Energy Sustainability*. ES 2010-90191, 1067-1076.

Eckelberry N D, Green M P, Fraser S A. (2010) Systems, Apparatus and Methods for Obtaining Intracellular Products and Cellular Mass and Debris from Algae and Derivative Products and Process of Use Thereof. International Patent Publication WO 2010-123903 published Oct. 28, 2010.

Elmore F E. (1904) A Process for Separating Certain Constituents of Subdivided Ores and like Substances, and Apparatus therefor." Great Britain Patent Application GB 13,578 filed Jun. 15, 1904.

Herrington R E, Fraim M. Method and Apparatus for Scale and Biofilm Control. United States Patent Publication US 2008-0156658 published Jul. 3, 2008.

Huebner J S, Arrieta R T. (2008) Sensing Device and Method Using Photo-Induced Charge Movements. U.S. Pat. No. 7,354,770 issued Apr. 8, 2008.

Huebner J S, Bowers D F, Mejia E N. (2009) Sensing Device and Method for Rapidly Determining Concentrations of Microbial Organisms Using Interfacial Photo-voltages. United States Patent Publication US 2009-0221025 published Sep. 3, 2009.

Hughes K D. (2010) Compact Culture Systems. United States Patent Publication US 2010-0218727 published Sep. 2, 2010.

Jervis E, Ramunas J. (2007) Cultured Cell and Method and Apparatus for Cell Culture. United States Patent Publication US 2007-0161106 published Jul. 12, 2007.

Joseph V, Huda A, Rogers J F. (2007) Temperature-Regulated Culture Plates. International Patent Publication WO 2007-092571 published Aug. 16, 2007.

Joseph V, Huda A, Rogers J F. (2010) Temperature-Regulated Culture Plates. United States Patent Publication US 2010-0009335 published Jan. 14, 2010.

Joseph V. (2008) Nutrient Perfusion Plate with Heater & Gas Exchange for High Content Screening. International Patent Publication WO 2008-118500 published Oct. 2, 2008.

Kameyama M, Kaneko N, Taki Y. (2010) Method for Producing Electronic Device and Electronic Device. U.S. Pat. No. 7,700,459 issued Apr. 20, 2010.

Maranhao A C A. (2010) Algae Photobioreactor. United States Patent Publication US 2010-0255569 published Oct. 7, 2010.

McCall J. (2008) Energy Production Systems and Methods. United States Patent Publication US 2008-0268302 published Oct. 30, 2008.

Merimon T, McCall J. (2010) System and Method for Continuous Fermentation of Algae. United States Patent Publication US 2010-0068791 published Mar. 18, 2010.

Mod K. (1990) Bioreactor Having a Gas Exchanger. U.S. Pat. No. 4,970,166 issued Nov. 13, 1990.

Noguera D R, Donohue T J, Anderson M A, McMahon K D, Tejedor I, Cho Y K, Perez R E. (2008) Light-Powered Microbial Fuel Cells. United States Patent Publication US 2008-0213632 published Sep. 4, 2008.

Poelman E, De Pauw N, Jeurissen B. (1997) Potential of electrolytic flocculation for recovery of micro-algae. *Resources, Conservation and Recycling.* 19, 1-10.

Posten C. (2009) Design principles of photo-bioreactors for cultivation of microalgae. *Eng. Life Sci.* 9(3), 165-177.

Raptis L. (1999) Electroporation Device and Method of Use. U.S. Pat. No. 6,001,617 issued Dec. 14, 1999.

Sathe S. (2010) Culturing and Harvesting Marine Microalgae for the Large-scale Production of Buiodiesel. MSE Thesis at The University of Adelaide, Australia.

Seebo H F. (2010) Algae High Density Bioreactor. United States Patent Publication US 2010-0162621 published Jul. 1, 2010.

Staples L S, Armstrong S M, Craigie J S, Bauder A G. (2003) Photobioreactor. Canadian Patent Application CA 2,394,518 published Jan. 23, 2003.

Su Z, Kang R, Shi S, Cong W, Cai Z. (2010) An Effective Device for Gas-Liquid Oxygen Removal in Enclosed Microalgae Culture. *Appl Biochem Biotechnol.* 160, 428-437.

Trösch W, Schmid-Stager U, Zastrow A, Retze A, Brucker F. (2003) Photobioreactor with Improved Supply of Light by Surface Enlargement, Wavelength Shifter Bars or Light Transport. U.S. Pat. No. 6,509,188 issue Jan. 21, 2003.

Uduman N, Qi Y, Danquah M K, Forde G M, Hoadley A. (2010) Dewatering of microalgal cultures: A major bottleneck to algae-based fuels. *Journal of Renewable and Sustainable Energy.* 2, 012701.

Xu L, Wang F, Li H-Z, Hu Z-M, Guob C, Liub C-Z. (2010) Development of an efficient electroflocculation technology integrated with dispersed-air flotation for harvesting-microalgae. *J Chem Technol Biotechnol.* 85, 1504-1507.

Xuan D T T. (2009) Harvesting marine algae for biodiesel feedstock. Report of 8 pages.

Yang R Y K, Bayraktar O, Pu H T. (2003) Plant-cell bioreactors with simultaneous electropermeabilization and electrophoresis. *Journal of Biotechnology.* 100, 13-22.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A photobioreactor for producing and harvesting microalgae, the photobioreactor comprising:

a vessel for cultivating microalgae, the vessel having at least one wall and an interior, at least a portion of the at least one wall being transparent to permit light of a frequency necessary to promote microalgae growth to enter into the interior of the vessel, an electrode consisting of at least part of the transparent portion of the at least one wall, said electrode comprising a layer of transparent conductive oxide selected from the group consisting of indium doped tin oxide, fluorine doped tin oxide, antimony doped tin oxide, zinc doped tin oxide, aluminum doped zinc oxide and a mixture thereof, the layer of transparent conducting oxide being transparent to light of the frequency necessary to promote microalgae growth and opaque to light of an infrared frequency range; and, a counter-electrode within the interior of the vessel, the counter-electrode being electrically connected to the layer of transparent conductive oxide for providing a potential difference across at least a portion of the interior of the vessel between the layer of transparent conductive oxide and the counter-electrode, with the proviso that the counter electrode is not a coating on a wall of the vessel.

2. The photobioreactor according to claim 1, wherein the counter-electrode comprises a metal, a conductive carbon, a transparent conducting oxide or a mixture thereof.

3. The photobioreactor according to claim 1, wherein the counter-electrode comprises aluminum, stainless steel or a transparent conducting oxide.

4. The photobioreactor according to claim 1, wherein the counter-electrode is an anode.

5. The photobioreactor according to claim 1 which is a tubular photobioreactor, wherein the vessel is cylindrical and the layer of transparent conducting oxide is coated on a curved surface of the cylindrical vessel.

6. The photobioreactor according to claim 1, wherein the vessel comprises glass, plastic, fiberglass or mixture thereof.

7. The photobioreactor according to claim 1, wherein the layer of transparent conductive oxide for use as an electrode is oriented vertically or horizontally and the counter-electrode is oriented vertically or horizontally.

8. The photobioreactor of claim 1 wherein the layer of transparent conductive oxide is applied at a thickness from about 0.01 μm to about 100 μm to said at least part of the transparent portion of the at least one wall.

9. The photobioreactor according to claim 1, wherein the counter-electrode comprises an inert coating.

10. The photobioreactor according to claim 1, wherein the counter-electrode is moveable.

11. The photobioreactor according to claim 1, which further comprises an electrical power source that is external of the interior of the vessel and that is electrically connected to the layer of transparent conductive oxide and to the counter electrode for providing a potential difference across at least a portion of the interior of the vessel between the layer of transparent conductive oxide and the counter-electrode.

12. A photobioreactor for producing and harvesting microalgae, the photobioreactor comprising:

a vessel for cultivating microalgae, the vessel having at least one wall and an interior, at least a portion of the at least one wall being transparent to permit light of a frequency necessary to promote microalgae growth to enter into the interior of the vessel, an electrode consisting of at least part of the transparent portion of the at least one wall, said electrode comprising a layer of transparent conductive oxide selected from the group consisting of indium doped tin oxide, fluorine doped tin oxide, antimony doped tin oxide, zinc doped tin oxide, aluminum doped zinc oxide and a mixture thereof, the layer of transparent conducting oxide being transparent to light of the frequency necessary to promote microalgae growth and opaque to light of an infrared frequency range;

a counter-electrode; and an electrical power source that is external of the interior of the vessel and that is electrically connected to the layer of transparent conductive oxide and to the counter electrode for providing a potential difference across at least a portion of the interior of the vessel between the layer of transparent conductive oxide and the counter-electrode.

13. The photobioreactor according to claim 12 which is a flat plate photobioreactor, wherein the vessel comprises a transparent first outer wall having the layer of transparent conductive oxide coated thereon and an opposed second outer wall having, the counter-electrode coated thereon.

14. The photobioreactor according to claim 13, wherein the counter-electrode is a layer of transparent conducting oxide coated on the second outer wall and the second outer wall is transparent.

15. The photobioreactor according to claim 12, wherein the counter-electrode comprises a metal, a conductive carbon, a transparent conducting oxide or a mixture thereof.

16. The photobioreactor according to claim 12, wherein the counter-electrode comprises aluminum, stainless steel or a transparent conducting oxide.

17. A method for producing and harvesting microalgae, the method comprising providing the photobioreactor of claim 1, introducing a cell culture medium and microalgae within the photobioreactor, growing the microalgae within the cell culture medium, and dewatering the microalgae electrochemically by applying a potential difference across at least a portion of the interior of the vessel of the photobioreactor between the layer of transparent conductive oxide and the counter-electrode.

18. The method according to claim 17, wherein applying the potential difference results in one electrode being a cathode and the other being an anode, and dewatering is accomplished by electroflotation in which the microalgae are floated to a surface of the cell culture medium by formation of gas bubbles at the anode due to electrolysis of water.

19. The method according to claim 17, wherein the dewatered microalgae is collected mechanically or chemically.

* * * * *